US006998114B2

(12) United States Patent  
Oldfield et al.

(10) Patent No.: US 6,998,114 B2
(45) Date of Patent: Feb. 14, 2006

(54) HAIR GROOMING FORMULATIONS AND METHODS FOR THE USE THEREOF

(75) Inventors: Terry Ann Oldfield, Kingsport, TN (US); Suzanne Winegar Dobbs, Kingsport, TN (US); Jessica Posey-Dowty, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 79 days.

(21) Appl. No.: 10/054,082

(22) Filed: Jan. 22, 2002

(65) Prior Publication Data

US 2003/0147829 A1 Aug. 7, 2003

(51) Int. Cl.  
A61K 7/06 (2006.01)  
A61K 7/00 (2006.01)

(52) U.S. Cl. ............... 424/70.13; 424/70.11; 424/401; 424/70.1

(58) Field of Classification Search ........... 424/61, 424/401, 70.13, 70.11, 70.1  
See application file for complete search history.

(56) References Cited

U.S. PATENT DOCUMENTS

| | | | |
|---|---|---|---|
| 3,734,874 A | 5/1973 | Kibler et al. | |
| 3,779,993 A | 12/1973 | Kibler et al. | |
| 4,158,053 A | 6/1979 | Greene et al. | |
| 4,233,196 A | 11/1980 | Sublett | |
| 4,300,580 A | * 11/1981 | O'Neill et al. | 132/203 |
| 4,335,220 A | 6/1982 | Coney | |
| 4,712,571 A | 12/1987 | Remz et al. | |
| 4,839,166 A | 6/1989 | Grollier et al. | |
| 4,876,083 A | 10/1989 | Grollier et al. | |
| 5,120,529 A | 6/1992 | Koch et al. | |
| 5,130,125 A | 7/1992 | Martin et al. | |
| 5,266,322 A | 11/1993 | Myers et al. | |
| 5,346,692 A | 9/1994 | Wohlrab et al. | |
| 5,380,520 A | 1/1995 | Dobbs | |
| 5,424,061 A | 6/1995 | Pappas et al. | |
| 5,512,273 A | 4/1996 | Martin | |
| 5,662,893 A | 9/1997 | George et al. | |
| 5,668,273 A | 9/1997 | Allen et al. | |
| 5,674,479 A | 10/1997 | George et al. | |
| 5,716,603 A | 2/1998 | Chen et al. | |
| 5,720,804 A | 2/1998 | Martin | |
| 5,741,901 A | 4/1998 | Cook et al. | |
| 5,747,019 A | 5/1998 | Weisman | |
| 5,785,958 A | 7/1998 | Sirdesai et al. | |
| 5,792,856 A | * 8/1998 | Allen et al. | 536/66 |
| 5,811,086 A | 9/1998 | Matsuzawa et al. | |
| 5,830,438 A | 11/1998 | Dupuis | |
| 5,871,573 A | 2/1999 | Cook et al. | |
| 5,922,312 A | 7/1999 | Jones et al. | |
| 5,955,063 A | 9/1999 | Brody et al. | |
| 5,981,738 A | 11/1999 | Cook et al. | |
| 5,994,530 A | * 11/1999 | Posey-Dowty et al. | 536/66 |
| 6,007,802 A | 12/1999 | Coffindaffer et al. | |
| 6,063,368 A | 5/2000 | Kapsner et al. | |
| 6,071,505 A | 6/2000 | Manuszak-Guerrini et al. | |
| 6,333,025 B1 | 12/2001 | Ramin | |
| 6,387,356 B1 | 5/2002 | Csernica et al. | |

OTHER PUBLICATIONS

Brody, D., "Water–Based Fingernail Coating", *Surface Coatings Australia*, Nov. 1998.  
*International Cosmetic Ingredient Dictionary and Handbook*, Eighth Edition, Cosmetic, Toiletry, and Fragrance Association, Inc., 1101 17th Street, N.W., Suite 300, Washington, D.C. 20036–4702.

* cited by examiner

Primary Examiner—Thurman K. Page  
Assistant Examiner—Blessing Fubara  
(74) Attorney, Agent, or Firm—Jonathan D. Wood; Bernard J. Graves, Jr.

(57) ABSTRACT

Disclosed are hair grooming compositions or formulations comprising at least one carboxyalkyl cellulose (CAC) ester such as carboxyalkyl cellulose acetate butyrate or acetate propionate and methods for the use thereof. The liquid compositions may be applied to hair in the form of a spray, mist, gel or mousse to facilitate styling of the hair.

3 Claims, No Drawings

HAIR GROOMING FORMULATIONS AND METHODS FOR THE USE THEREOF

FIELD OF THE INVENTION

This invention pertains to hair grooming compositions or formulations and methods for the use thereof. More specifically, this invention pertains to novel film-forming formulations comprising at least one carboxyalkyl cellulose (CAC) ester which may be applied to hair to in the form of a spray, mist, gel or mousse to facilitate styling of the hair.

BACKGROUND OF THE INVENTION

Hair spray formulations typically comprise a solution or dispersion of a polymer (the fixative) in water/alcohol mixtures. The polymeric materials which are soluble or dispersible in water, alcohol or mixtures thereof and are typically used in hair spray formulations are derived from one or more vinyl monomers such as vinyl acetate; crotonic, acrylic and/or methacrylic acids and/or their esters; N-vinylpyrrolidinone; octylacrylamide; and/or styrene compounds. When applied to hair and allowed to dry, the polymeric material provides human hair with body, consistency, firm texture, and, in general, maintains the hair in a desired arrangement. Hair spray formulations normally contain significant amounts of volatile organic compounds such as alcohols to facilitate rapid drying of the polymer solution. Environmental concerns continue to encourage the development of hair spray formulations which contain low levels of volatile organic compounds. Attempts to omit the volatile organic component of conventional hair sprays have failed to produce formulations which have acceptable drying times, particularly when the water level exceeds about 60 weight percent of the formulation.

Hair styling and grooming compositions containing higher levels of water typically contain as the film-former or fixative one or more of the following: acrylic or vinyl resins, water-dispersible polyesters, or polyurethanes. For example, U.S. Pat. No. 4,300,580 describes hair spray formulations comprising a water-dispersible (or water-dissipatible), linear polyester fixative in a water/alcohol mixture. These formulations are fast drying and have good hair-holding properties but also possess the disadvantage of being difficult to remove from the hair. In an effort to overcome the fixative removal problem, U.S. Pat. No. 4,300,580 discloses the addition of certain water soluble polymers, such as poly (ethylene glycols), to formulations containing a water-dispersible, linear polyester.

Very few of the known hair styling compositions contain a hair fixative material or resin, i.e., a film-forming material, that is based on cellulose. In instances where cellulose derivatives are used as hair fixatives, the cellulose derivative has been a quaternized, cationic cellulose derivative. The use of cationic cellulose derivatives as the fixative and/or conditioning agent in hair grooming formulations is disclosed in U.S. Pat. Nos. 6,071,505; 6,063,368; 6,007,802; 5,922,312; 5,830,438; 5,811,086; 4,876,083; and 4,839,166.

U.S. Pat. Nos. 5,668,273 and 5,792,856 describe certain $C_2$–$C_4$ alkanoate esters carboxy($C_1$–$C_3$ alkyl) cellulose, processes for the preparation thereof, and coating compositions, including waterborne coating compositions, containing one of the disclosed carboxy($C_1$–$C_3$ alkyl) cellulose esters. U.S. Pat. No. 5,994,530 describes aqueous pigment dispersions comprising a pigment and a $C_2$–$C_4$ alkanoate esters carboxy($C_1$–$C_3$ alkyl) cellulose.

BRIEF SUMMARY OF THE INVENTION

We have found that partially-neutralized, $C_2$–$C_4$ alkanoate esters carboxy($C_1$–$C_3$ alkyl) cellulose are useful fixatives or film-formers when used in hair grooming compositions selected from sprays, gels and mousses. Thus, one embodiment of the present invention pertains to a hair grooming composition comprising:

(1) about 0.5 to 10 weight percent of a partially or totally neutralized carboxyalkyl cellulose ester; and
(2) about 85 to 99.5 weight percent of a liquid vehicle comprising about 0 to 96 weight percent water and about 4 to 100 weight percent of an alkanol having 2 or 3 carbon atoms;

wherein the carboxyalkyl cellulose ester of component (1) is a $C_2$–$C_4$ alkanoate ester of carboxy($C_1$–$C_3$-alkyl) cellulose having an inherent viscosity of about 0.2 to 0.7 dL/g as measured in a 60/40 by weight solution of phenol/tetrachloroethane at 25° C., a degree of substitution per anhydroglucose unit of carboxy($C_1$–$C_3$-alkyl) of greater than 0.2 to about 0.75, and a degree of substitution per anhydroglucose unit of $C_2$–$C_4$ alkanoate ester residue of about 1.5 to 2.7; and about 40 to 90 mole percent of the carboxy groups of the carboxyalkyl cellulose ester of component (1) are neutralized with a base.

A second embodiment of our invention is directed to a hair grooming composition comprising:

I. about 0.5 to 10 weight percent of a partially or totally neutralized carboxyalkyl cellulose ester;
II. about 0.5 to 10 weight percent of a sulfonate-containing, linear polyester; and
III. about 85 to 99 weight percent of a liquid vehicle comprising about 0 to 96 weight percent water and about 4 to 100 weight percent of an alkanol having 2 or 3 carbon atoms;

wherein the partially or totally neutralized, carboxyalkyl cellulose ester is defined above; and the sulfonate-containing, linear polyester is comprised of:

(i) diacid monomer residues comprising residues of at least one dicarboxylic acid;
(ii) about 4 to 26 mole percent, based on the total of all acid, hydroxy and amino equivalents, of monomer residues of at least one difunctional sulfo monomer containing at least one sulfonate group bonded to an aromatic ring where the functional groups are hydroxy, carboxy or amino; and
(iii) monomer residues of at least one diol or a mixture of a diol and diamine comprising:
  (a) at least 15 mole percent, based on the total mole percent of diol monomer residues or diol and diamine monomer residues, of a diol having the formula —(OCH$_2$CH$_2$)$_n$— wherein n is 2 to about 10; or
  (b) about 0.1 to less than about 15 mole percent, based on the total mole percent of diol monomer residues or diol and diamine monomer residues, of monomer residues of a poly(ethylene glycol) having the formula —(OCH$_2$CH$_2$)$_n$— wherein n is 2 to about 500, provided that the mole percent of such residues is inversely proportional to the value of n; and, optionally
(iv) monomer residues of at least one difunctional monomer reactant selected from hydroxycarboxylic acids, aminocarboxylic acids and aminoalkanols;

provided that at least 20% of the groups linking the monomeric units are ester, i.e., carbonyloxy linkages.

A third embodiment of our invention pertains to a method for grooming or styling hair comprising the steps of:
(i) arranging the hair in a desired manner;
(ii) applying to the hair the hair grooming composition defined above; and (iii) allowing the applied hair grooming composition to dry to produce a coating of the partially or totally neutralized carboxyalkyl cellulose ester contained in the hair grooming composition on at least a portion of the hair.

The order of step (i), (ii) and (iii) may be varied depending on the particular hair grooming composition being used. For example, when grooming or styling hair using a hair spray, the grooming normally will be performed by a sequence of steps (i), (ii) and (iii) whereas a gel or mousse normally will be used in the order of steps (ii), (i) and (iii). The hair grooming formulation provided by the present invention provides a non-tacky film upon drying on hair and possess a lower pH than traditional acrylic resins at similar levels of neutralization, providing greater compatibility with other pH sensitive resins or polymeric materials that may be included in the hair grooming formulations. The hair spray formulations may be applied to hair using either a pump or an aerosol spray.

DETAILED DESCRIPTION OF THE INVENTION

The preparation of the $C_2$–$C_4$ alkanoate esters of carboxy ($C_1$–$C_3$-alkyl) cellulose component of the novel hair grooming compositions of the present invention is described in detail in U.S. Pat. Nos. 5,668,273 and 5,792,856. The carboxyalkyl cellulose esters have a high combined degree of substitution (DS) per anhydroglucose unit on the cellulose backbone of ether and ester functions in the trisubstituted or partially hydrolyzed form, typically less than about 0.90 DS hydroxyl. More specifically, the carboxyalkyl cellulose esters have an inherent viscosity of 0.20 to 0.70 dL/g, preferably 0.30 to 0.60 dL/g, as measured in a 60/40 by weight solution of phenol/tetrachloroethane at 25° C., a degree of substitution per anhydroglucose unit of carboxy ($C_1$–$C_3$ alkyl) of about 0.20 to 0.75, and a degree of substitution per anhydroglucose unit of $C_2$–$C_4$ alkanoate ester residues, i.e., acetate, propionate and/or butyrate, of about 1.5 to about 2.7, and a degree of substitution per anhydroglucose unit of hydroxyl of about 0.1 to 0.9, preferably 0.1 to 0.7.

The $C_2$–$C_4$ alkanoate esters of carboxy($C_1$–$C_3$-alkyl) cellulose component of our novel hair grooming compositions preferably is a carboxymethyl cellulose acetate butyrate or carboxymethyl cellulose acetate propionate having a degree of substitution of carboxymethyl of 0.2 to 0.75, preferably 0.25 to 0.35, a degree of substitution per anhydroglucose unit of hydroxyl from about 0.1 to 0.9, and a degree of substitution per anhydroglucose unit of butyryl or propionyl of about 0.1 to 2.6 and a degree of substitution per anhydroglucose unit of acetyl of 0.1 to 1.65, and having an inherent viscosity of 0.2 to 0.7 dL/g, as measured in a 60/40 by weight solution of phenol/tetrachloroethane at 25° C. The carboxymethyl cellulose acetate butyrates or propionates preferably have an inherent viscosity of 0.30 to 0.60 dL/g, a degree of substitution per anhydroglucose unit of hydroxyl of 0.10 to 0.70, a degree of substitution per anhydroglucose unit of butyryl or propionyl of 1.1 to 2.55, and a degree of substitution per anhydroglucose unit of acetyl is 0.1 to 0.9.

The $C_2$–$C_4$ alkanoate esters of carboxy($C_1$–$C_3$-alkyl) cellulose present in our novel hair grooming compositions are partially neutralized with a base, e.g., about 40 to 90 mole percent, preferably 50 to 80 mole percent of the carboxy groups are neutralized with a base such as sodium and potassium carbonate, ammonium hydroxide and amines. The base preferably is an amine, preferably an alkanolamine, and most preferably an alkanolamine having a molecular weight of about 45 to 200. Examples of the alkanolamines include monoethanolamine, diethanolamine, triethanolamine dimethyl(ethanol)amine, 2-amino-2-methylpropanol (AMP), monoisopropanolamine, triisopropanolamine, and combinations thereof. The degree of neutralization, i.e., the mole percentage of carboxy groups that are neutralized with base, may vary depending on other ingredients that may be present in the hair grooming composition, the composition of the liquid vehicle component of the hair grooming composition and the intended function and/or performance characteristics of the hair care composition. Normally, the degree of neutralization is from about 20 to 90 mole percent, preferably from about 40 to 80 mole percent The most preferred neutralization is from about 50 to 80%.

The liquid vehicle component of the hair grooming compositions of the present invention comprises about 0 to 96 weight percent water and about 4 to 100 weight percent of an alkanol having 2 or 3 carbon atoms, preferably about 20 to 90 weight percent water and about 10 to 80 weight percent of an alkanol having 2 or 3 carbon atoms. Although it is possible for the hair grooming compositions to contain other organic solvents such as certain ketones, alkyl esters of alkanoic acids containing a total of from about 3 to 6 carbon atoms, ethanol, propanol and 2-propanol are the preferred organic solvents with ethanol being the most preferred.

When the hair grooming compositions are used in the form of an aerosol spray, the aerosol formulation will include a propellant. The propellant may be any liquefiable gas conventionally used for aerosols. Examples of materials that are suitable for use as propellants are chlorodifluoromethane, 1,1-difluoroethane, monochlorodifluoromethane, dimethyl ether, $C_1$–$C_4$ hydrocarbons such as methane, ethane, propane, n-butane, and isobutane, and mixtures thereof. Water-soluble gases such as dimethyl ether, carbon dioxide, and/or nitrous oxide also may be used to obtain aerosols having reduced flammability. Preferably, the propellant is a $C_1$–$C_4$ aliphatic hydrocarbon, 1,1-difluoroethane, dimethyl ether, or combinations thereof. The amount of propellant typically is from about 5 to 60 weight percent, preferably from about 10 to 45 weight percent, based on the total weight of the composition.

The hair grooming formulations of this invention also may contain conventional hair care adjuvants known in the art in amounts which may constitute up to about 20 weight percent, more typically up to about 10 weight percent, of the total weight of the formulation. Such adjuvants preferably constitute from about 0.01 to about 10 weight percent of the total weight of the hair care formulation. Examples of adjuvants include, but are not limited to, plasticizers, coalescing agents, silicones, emollients, emulsifiers, lubricants and penetrants such as various lanolin compounds, protein hydrolysates, or other protein derivatives, viscosity increasing and decreasing agents, ethylene adducts and polyoxyethylene cholesterol, dyes, tints and other colorants, perfumes or fragrances, preservatives, antifoaming agents, chelating agents, polymers and resins, hair conditioners, and the like.

A plasticizer or a coalescing agent may be added to modify the film-forming characteristics of the hair grooming formulations of the present invention. The plasticizer or coalescing agent may be present in amounts up to about 5 weight percent, preferably from about 0.01 to about 2 weight percent. Examples of plasticizers include, but are not limited to, glycols, adipate esters, citrate esters, phthalate esters, epoxidized vegetable oils, glycerine as well as polymeric plasticizers. More preferred plasticizers in accordance with the invention are, for example, di-(2-ethylhexyl) adipate, dibutyl phthalate, dibutyl adipate, diethyl phthalate, diisobutyl adipate, diisononyl adipate, n-butyl benzyl phthalate, 1,3-butylene glycol/adipic acid polyester, tricresyl phosphate, benzyl benzoate, triphenyl phosphate, butyl stearate, triethyl citrate, tributyl citrate, tributyl acetyl citrate, camphor, epoxidized soybean oil, propylene glycol adipate, 2,2,4-trimethyl-1,3-pentanediol diisobutyrate, 2-amino-2-methyl propanol, and dibutyl sebacate. Other plasticizers include: Dimethicone copolyol, PEG-6 capric/caprylic glyceride, phenyl trimethicone, propylene glycol, and dipropylene glycol.

The hair grooming compositions provided by the present invention also may contain other polymers or resins typically used in hair care formulations. Examples of these polymers or resins include, but are not limited to, the ethyl, isopropyl, or n-butyl esters of poly(methyl vinyl ether/maleic acid), polyvinyl pyrrolidinone (PVP), polyvinyl caprolactam, polyvinyl pyrrolidinone/vinyl acetate, copolymers of vinyl pyrrolidinone and methyl methacrylate, copolymers of acrylic acid, methacrylic acid, and their esters, poly(ethyl acrylate/acrylic acid/N-tert-butyl acrylamide), PVP/ethyl methacrylate/methacrylic acid terpolymer, PVP/vinylcaprolactam/dimethylaminopropyl methacrylamide terpolymer, poly(vinyl acetate/crotonic acid), vinyl acetate/crotonates/vinyl neodecaoate copolymer, polyvinyl acetate (PVA), copolymers of PVA and crotonic acid, copolymers of PVA and maleic anhydride, hydroxypropyl cellulose, hydroxypropyl methylcellulose, hydroxypropyl guar gum, sodium polystyrene sulfonate, octylacrylamide/acrylate/butylaminoethyl methacrylate copolymers, sulfopolyesters, and mixtures of such polymers or resins.

A preferred polymer which may be used as a fixative or film-forming component in combination with the $C_2$–$C_4$ alkanoate ester of carboxy($C_1$–$C_3$-alkyl) cellulose component of the hair grooming compositions is a sulfonate-containing, water dispersible (or water-dissipatible), linear polyester. The relative amounts of the $C_2$–$C_4$ alkanoate ester of carboxy($C_1$–$C_3$-alkyl) cellulose and the sulfonate-containing, linear polyester can be varied widely, e.g., weight ratios of 90:10 to 5:95, preferably from 70:30 to 10:90. The sulfonate-containing, linear polyesters useful in the present invention are described in U.S. Pat. Nos. 3,734,874, 3,779,993, 4,233,196, 4,335,220, 5,662,893 and 5,674,479. These polyesters are soluble or dispersible in the liquid vehicle of the hair grooming compositions of the present invention. The sulfonate-containing, linear polyesters have an inherent viscosity of at least 0.1 dL/g, preferably about 0.24 to 0.38 dL/g, when measured at 25° C. using 0.25 g polymer per 100 ml of a solvent consisting of 60 parts by weight phenol and 40 parts by weight tetrachloroethane.

The sulfonate-containing, linear polyesters are comprised of:
(i) diacid monomer residues comprising residues of at least one dicarboxylic acid;
(ii) about 4 to 26 mole percent, based on the total of all acid, hydroxy and amino equivalents, of monomer residues of at least one difunctional sulfo monomer containing at least one sulfonate group bonded to an aromatic ring where the functional groups are hydroxy, carboxy or amino; and
(iii) monomer residues of at least one diol or a mixture of a diol and diamine comprising:
(a) at least 15 mole percent, based on the total mole percent of diol monomer residues or diol and diamine monomer residues, of a diol having the formula —(OCH$_2$CH$_2$)$_n$— wherein n is 2 to about 10; or
(b) about 0.1 to less than about 15 mole percent, based on the total mole percent of diol monomer residues or diol and diamine monomer residues, of monomer residues of a poly(ethylene glycol) having the formula —(OCH$_2$CH$_2$)$_n$— wherein n is 2 to about 500, provided that the mole percent of such residues is inversely proportional to the value of n; and, optionally
(iv) monomer residues of at least one difunctional monomer reactant selected from hydroxycarboxylic acids, aminocarboxylic acids and aminoalkanols;
provided that at least 20% of the groups linking the monomeric units are ester, i.e., carbonyloxy, linkages.

The sulfonate-containing, linear polymers thus comprise polyesters, including polyester-amides, consisting of repeating, alternating residues of (1) one or more dicarboxylic acids and (2) one or more diols or a combination of one or more diols amd one or more diamines where, in the preceding definition, the mole percentages are based on 100 mole percent dicarboxylic acid residues and 100 mole percent diol, or diol and diamine, residues. Alternatively, the polymers may include residues of monomers having mixed functionality such as hydroxycarboxylic acids, aminocarboxylic acids and/or amino alkanols. The residues of component (i) may be derived from one or more dicarboxylic acids or their ester-forming derivatives such as dialkyl ester, bis(hydroxyalkyl) esters, acid chlorides, or, in some cases, anhydrides. The sulfonate group of component (ii) may be an alkali metal sulfonic acid salt such as lithium, potassium or, preferably, sodium sulfonate groups.

The preferred sulfonate-containing, linear polyesters have an inherent viscosity of about 0.24 to 0.38 dL/g and are comprised of:
(i) diacid monomer residues comprising about 75 to 84 mole percent isophthalic acid residues and about 16 to 26 mole percent 5-sodiosulfo-isophthalic acid residues; and
(ii) diol monomer residues comprising about 45 to 90 mole percent diethylene glycol residues and about 55 to 10 mole percent ethylene glycol residues, 1,4-cyclohexanedimethanol residues or mixtures thereof.

Specific embodiments of these sulfonate-containing, linear polyesters are available from Eastman Chemical Company in the form of pellets under the names EASTMAN AQ 38S, 48 Ultra, and 55S polymers.

Our novel hair grooming compositions also may contain a conditioner in amounts up to about 10 weight percent, preferably from about 0.01 to 10 weight percent, and more preferably from about 0.1 to 5 weight percent, based on the total weight of the hair grooming composition. Typical conditioners include, for example, a non-volatile silicone compound or a mixture of a low molecular weight polydimethylsiloxane fluid and a higher molecular weight polydimethylsiloxane gum. The non-volatile polydimethylsiloxane mixture may be added to a hair care formulation of the invention in an amount sufficient to provide improved combing and improved feel (softness) to the hair after shampooing.

Other conditioning agents also may be incorporated into the hair grooming compositions of the present invention. These agents include, for example, polysiloxane polyether copolymers, acetylated lanolin alcohols, lauryl dimethylamine oxide, a lanolin-derived sterol, lanolin alcohol, an isopropyl ester of lanolin fatty acid, keratin and collagen amino acids, stearamidopropyl dimethylamine, a polyol fatty acid, guar, hydroxypropyl-trimethyl ammonium chloride, cetyl/stearyl alcohol, keratin protein derivatives, an amino functional silicone, ethoxylated (30) castor oil, acetylated lanolin alcohol, fatty alcohol fraction of lanolin, a mineral oil and lanolin alcohol mixture, high molecular weight ester of lanolin, N-vinylpyrrolidone/dimethylaminoethyl methacrylate copolymer, ethylene oxide adducts of soya sterol, stearic acid ester of ethoxylated methyl glucoside, sodium salt of polyhydroxycarboxylic acid, hydroxylated lanolin, cocamidopropyl (dimethyl) amine lactate, cocamidopropyl(dimethyl) amine propionate, cocamidopropylmorpholine lactate, isostearamidopropyl dimethylaminelactate, isostearamidopropyl morpholine lactate, oleamidopropyl dimethylamine lactate, linoleamidopropyl dimethylamine lactate, ethylene glycol monostearate and propylene glycol mixture, stearamidopropyl dimethylamine lactate, acetamide monoethanolamine, lactamide monoethanolamine, stearamide monoethanolamine, behenalkonium chloride, a behenyl trimethyl ammonium methosulfate and cetearyl alcohol mixture, cetearyl alcohol, tallow imidazaolinum methosulfate, mixed ethoxylated and propoxylated long chain alcohols, oleamine oxide, stearamide oxide, soya ethyldiammonium ethosulfate, ricinolamidopropyl ethyldimonium ethosulfate, N-(3-isostearamidopropyl)-N,N-dimethyl amino glycolate, N-(3-isostearamidopropyl)-N,N-dimethyl amino gluconate, hydrolyzed animal keratin, ethyl hydrolyzed animal keratin, stearamidoethyl diethylamine, cocamidopropyl dimethylamine, lauramidopropyl dimethylamine, oleamidopropyl dimethylamine, palmitamidopropyl dimethylamine, avocado oil, sweet almond oil, grape seed oil, jojoba oil, apricot kernel oil, sesame oil, safflower oil, wheat germ oil, ricinoleamidodimethyl amine lactate, wheat germamido dimethylamine lactate, wheat germamidopropyl dimethylamine oxide, disodium isostearamido monoethanolamine sulfosuccinate, disodium oleamide PEG-2 sulfo succinate, disodium oleamide monoethanolamine sulfosuccinate, disodium ricinoleyl monoethanolamine sulfosuccinate, disodium wheat germamido monoethanolamine sulfosuccinate, disodium wheat germamido PEG-2 sulfosuccinate, polyethylene glycol and distearates, synthetic calcium silicate, isostearic alkanolamide, ethyl ester of hydrolyzed animal protein, blend of cetyl and stearyl alcohol with ethoxylated cetyl or stearyl alcohol, propoxylated lanolin alcohol, isostearamide diethanolamine, and hydrolyzed collagen protein.

The hair grooming compositions also may contain other adjuvants to render such compositions more acceptable for use in hair care. These adjuvants include emulsifiers such as ethoxylated fatty alcohols and esters, ethoxylated glycerides, dimethicone copolyol esters, glyceryl esters, hydrogenated fatty glycerides, and the sodium salts of fatty acids; preservatives such as benzyl alcohol, methyl paraben, propyl paraben and imidazolidinylurea; viscosity increasing agents such as methyl vinyl ether/maleic anhydride copolymer crosslinked with 1,9-decadiene, carbomers, acrylates/alkyl acrylate crosspolymers, the diethanolamide of a long chain fatty acid, fatty alcohols (for example, stearyl alcohol), cellulose gum, sodium chloride, and sodium sulfate; and viscosity decreasing agents such as ethyl alcohol (if not present in the vehicle), glycerin, propylene glycol, and ethoxydiglycol. The pH of a hair care formulation may be adjusted using pH adjusting agents such as citric acid, succinic acid, sodium hydroxide, and triethanolamine. Colorants which may be included in the compositions include, for example, any of the Food, Drug and Cosmetics (FD&C) or Drug and Cosmetics (D&C) dyes. Hair oxidizing (bleaching) agents such as hydrogen peroxide, perborate salts, persulfate salts, and percarbonate salts may also be used. Hair reducing agents such as thioglycolates, represent another type of adjuvant. Perfume oils are also commonly found in hair care products and may be used here. Chelating agents, such as ethylenediamine tetraacetic acid (EDTA), may also be used.

EXAMPLES

The preparation and use of the hair grooming compositions provided by the present invention are further illustrated by the following examples. All percentages given in the examples are by weight unless otherwise specified. The carboxy($C_1$–$C_3$-alkyl) cellulose ester used in the examples was a carboxymethyl cellulose acetate butyrate (CMCAB) having an inherent viscosity of 0.41 dL/g, a degree of substitution per anhydroglucose unit of hydroxyl of 0.63, a degree of substitution per anhydroglucose unit of butyryl of 1.63, and a degree of substitution per anhydroglucose unit of acetyl of 0.43.

Example 1–10

Several hair grooming compositions according to the present invention were prepared and are described in Table I. The compositions of Examples 1–3 were prepared by dissolving a neutralizing agent, AMP-95 (95% 2-amino-2-methyl-1-propanol from Angus Chemical Company) in ethanol in the concentration shown in Table I. The CMCAB was added slowly to the AMP/ethanol solution with rapid stirring. The CMCAB dissolved, resulting in a clear solution of 10% CMCAB in the AMP/ethanol solution. Each composition was drawn down on a glass plate to make a film. After drying, the films were clear and continuous. Water resistance of the films was determined by dropping water on the film surface, then wiping with a paper towel. Under these conditions the films were unaffected. Soap and warm water were then applied to the films with scrubbing. The water and scrub resistance exhibited by the films indicate that compositions 40 mole percent neutralized (Mole % Neut'n in Table I) may be difficult to remove from hair and, therefore, may be unacceptable hair spray formulations. The samples neutralized 60 and 80 mole percent exhibit water resistance properties which would cause films of the compositions to be readily removed from hair upon shampooing.

Examples 4–6 were prepared by diluting samples from Examples 1–3, respectively, with water to decrease the concentrations of CMCAB, AMP-95 and ethanol as reported in Table I. Turbidity was measured on these samples using the Hach Model 2100N IS turbidimeter and the turbidity values are reported as Nephelometric Turbidity Units (NTU) in Table I. The results shown in Table I show that turbidity decreases with increasing neutralization. The pH was measured using a Corning glass/combination electrode and pH Meter Model 350. The composition of Example 6 was sprayed onto a hair tress. During drying, the hair tress did not become tacky. After the hair tress was dry, the hair felt stiff and had an excellent appearance. The hair spray composition combed out of the hair easily without flaking.

Examples 7–10 were prepared by dissolving AMP-95 in ethanol, then mixing in CMCAB until dissolved. Water then was mixed in, and more ethanol was added to achieve the ethanol concentration given in Table I. Turbidity and viscosity measurements show that decreasing the ethanol content of the formulation increases turbidity and viscosity. Viscosity measurements, given in Table 1 in centipoise, were obtained using a Brookfield Viscometer Model LV, Spindle 2 at 60 RPM.

Films prepared from all of the above compositions demonstrate that ethanol levels less than about 30% can produce hazy films if a coalescing agent is not present. At high levels, AMP functions as a coalescing agent, as well as being a neutralizing agent.

TABLE I

| Example No. | Concentration | | | Mole % Neut'n | pH | Turbidity | Viscosity |
|---|---|---|---|---|---|---|---|
| | CMCAB | AMP-95 | Ethanol | | | | |
| 1 | 10 | 0.40 | 89.8 | 40 | NA | ND | ND |
| 2 | 10 | 0.60 | 89.6 | 60 | NA | ND | ND |
| 3 | 10 | 0.80 | 89.2 | 80 | NA | ND | ND |
| 4 | 6.0 | 0.24 | 53.6 | 40 | 5.4 | 152 | ND |
| 5 | 6.0 | 0.36 | 53.6 | 60 | 5.9 | 49 | 21 |
| 6 | 6.0 | 0.48 | 53.5 | 80 | 6.4 | 38 | ND |
| 7 | 5.0 | 0.40 | 30.1 | 80 | 6.5 | 187 | 202 |
| 8 | 5.0 | 0.40 | 20.1 | 80 | 6.6 | >1000 | 1042 |
| 9 | 5.0 | 0.45 | 30.0 | 90 | 7.4 | 144 | 187 |
| 10 | 5.0 | 0.45 | 20.0 | 90 | 7.5 | >1000 | 1280 |

NA: Not applicable
ND: Not determined

Example 11

This example demonstrates the compatibility of the hair grooming compositions of the present invention with sulfonate-containing, linear polyester as represented by EASTMAN AQ 48 sulfopolyester. The following ingredients were mixed in the order given: 10 g of a 30% AQ 48 dispersion in 31.8 g water, 28.2 g ethanol, and 30 g of the composition of Example 3. This gave a hair grooming composition containing the following amounts of materials:

| | |
|---|---|
| CMCAB | 3.0% |
| AQ 48 polymer | 3.0% |
| AMP-95 | 0.24% |
| Ethanol | 55.0% |
| Water, q.s. to | 100.0% |

The initial pH of the composition was 6.2 and turbidity was 17 NTU. The formulation was aged at 45° C. for 3 months, then at room temperature for 1 month. After aging under these conditions, the pH of the composition was 5.9 and turbidity was 19 NTU. A film was prepared from the formulation on a glass plate prior to aging. After drying, the film appeared clear and adhered to the glass plate.

Comparative Example 1

This example demonstrates the use of Eastman AQ 48 sulfonate-containing polyester in combination with an N-octylacrylamide/acrylates/butylaminoethyl methacrylate polymer marketed as Balance 47 by National Starch). The following ingredients were mixed in the order given:

| | |
|---|---|
| 30% AQ 48 dispersion in water | 13.3 g |
| Water | 30.5 g |
| Ethanol | 55.0 g |
| AMP-95 | 0.19 g |
| Balance 47 polymer | 1.0 g |

The amount of AMP-95 used gave 80% neutralization of the Balance 47 polymer. Initial pH of the mixture was 8.0; turbidity was 4.5 NTU. The formulation was aged at 45° C. for 3 months, then at room temperature for 1 month. After aging under these conditions, the pH was 7.2 and turbidity was 34 NTU. This example shows that at the same degree of neutralization as in Example 11, this formulation with Balance 47 polymer becomes cloudy upon aging at elevated temperature whereas the formulation in Example 11 with CMCAB does not. This result can be attributed to the lower initial pH of the formulation in Example 11, and the greater stability of Eastman AQ 48 sulfonate-containing polyester at the lower pH.

Example 12

This example demonstrates the use of CMCAB in an aerosol hair spray formulation. In a glass aerosol container, dimethyl ether propellant (21.0 g) was added to a portion (39.0 g) of the composition given in Example 7. After mixing, the aerosol hair spray composition was sprayed onto a hair tress and onto a glass plate. The mixture atomized very well and had a good appearance on the hair. The film sprayed onto the glass plate was slightly hazy after drying. To produce a clear film, a coalescing aid such as ethoxydiglycol, dipropylene glycol, or a dimethicone copolyol may be added to the formulation.

The preceding description demonstrates that partially-neutralized, $C_2$–$C_4$ alkanoate esters carboxy($C_1$–$C_3$ alkyl) cellulose are useful fixatives or film-formers when used in hair grooming compositions. Partially-neutralized, $C_2$–$C_4$ alkanoate esters carboxy($C_1$–$C_3$ alkyl) cellulose may be used in other hair grooming compositions such as hair gels. Such a hair gel is exemplified by the following composition:

Part A—A gel was prepared by sprinkling 0.50 g Stabileze QM into 99.2 g water and stirring at 65 to 70° C. for 45 minutes. Stabileze QM is a gelling agent consisting of a methyl vinyl ether/maleic anhydride copolymer marketed by ISP. The mixture was cooled and 0.32 g AMP-95 was added with stirring to produce a clear gel.

Part B-A 20% solution of CMCAB (having the same composition as the CMCAB used in Examples 1–10) was prepared by dissolving CMCAB in ethanol. AMP-95 was added to neutralize the CMCAB to a degree of 80%.

Part A above (30.0 g) was weighed into a beaker and Part B (10.0 g) was added with stirring. The gel became stiffer and cloudy. Part A above and the combined Part A/Part B were applied to hair tresses. The hair tresses were combed and hung to dry. After drying, both tresses were very stiff; but after bending and pressing the tresses with the fingers, the tress coated with Part A/Part B remained stiffer than the tress coated with Part A only.

Another hair gel was prepared from the following components: Carbopol Ultrez 10 (0.48 g; a carbomer marketed by BF Goodrich was sprinkled into 79.28 g water and stirred at room temperature. When the white particles of the Carbopol Ultrez 10 had disappeared, 20.0 g of Part B described above was added slowly. As the CMCAB solution was added, the mixture began to thicken to gel consistency. Triethanolamine (0.24 g) was added last to continue neutralization and to produce a cloudy gel of greater stiffness. The mixture was applied to a hair tress, which was then wrapped on a mandrel and dried overnight. When the hair tress was removed from the mandrel, the hair formed a stiff curl.

The invention has been described in detail with particular reference to preferred embodiments thereof, but it will be understood that variations and modifications can be effected within the spirit and scope of the invention.

We claim:

1. A hair grooming composition comprising:
   I. about 0.5 to 10 weight percent of a partially or totally neutralized carboxyalkyl cellulose ester;
   II. about 0.5 to 10 weight percent of a sulfonate-containing, linear polyester; and
   III. about 85 to 99 weight percent of a liquid vehicle comprising about 0 to 96 weight percent water and about 4 to 100 weight percent of an alkanol having 2 or 3 carbon atoms;
   wherein
   the carboxyalkyl cellulose ester of component (I) is a $C_2$–$C_4$ alkanoate ester of carboxy($C_1$–$C_3$-alkyl) cellulose having an inherent viscosity of about 0.2 to 0.7 dL/g as measured in a 60/40 by weight solution of phenol/tetrachloroethane at 25° C., a degree of substitution per anhydroglucose unit of carboxy($C_1$–$C_3$-alkyl) of greater than 0.2 to about 0.75, and a degree of substitution per anhydroglucose unit of $C_2$–$C_4$ alkanoate ester residue of about 1.5 to 2.7;
   about 40 to 90 mole percent of the carboxy groups of the carboxyalkyl cellulose ester of component (I) are neutralized with a base; and the sulfonate-containing, linear polyester is comprised of:
   (i) diacid monomer residues comprising residues of at least one dicarboxylic acid;
   (ii) about 4 to 26 mole percent, based on the total of all acid, hydroxy and amino equivalents, of monomer residues of at least one difunctional sulfo monomer containing at least one sulfonate group bonded to an aromatic ring where the functional groups are hydroxy, carboxy or amino; and
   (iii) monomer residues of at least one diol or a mixture of a diol and diamine comprising:
      (a) at least 15 mole percent, based on the total mole percent of diol monomer residues or diol and diamine monomer residues, of a diol having the formula —(OCH$_2$CH$_2$)$_n$— wherein n is 2 to about 10; or
      (b) about 0.1 to less than about 15 mole percent, based on the total mole percent of diol monomer residues or diol and diamine monomer residues, of monomer residues of a poly(ethylene glycol) having the formula —(OCH$_2$CH$_2$)$_n$— wherein n is 2 to about 500, provided that the mole percent of such residues is inversely proportional to the value of n; and, optionally
   (iv) monomer residues of at least one difunctional monomer reactant selected from hydroxycarboxylic acids, aminocarboxylic acids and aminoalkanols;
   provided that at least 20% of the groups linking the monomeric units are carbonyloxy ester linkages.

2. A hair grooming composition according to claim 1 wherein the $C_2$–$C_4$ alkanoate ester of carboxy($C_1$–$C_3$-alkyl) cellulose component is a carboxymethyl cellulose acetate butyrate having an inherent viscosity of 0.30 to 0.60 dL/g, a degree of substitution per anhydroglucose unit of hydroxyl of 0.10 to 0.70, a degree of substitution per anhydroglucose unit of butyryl of 1.1 to 2.55, and a degree of substitution per anhydroglucose unit of acetyl is 0.1 to 0.9; the liquid vehicle comprises about 20 to 90 weight percent water and about 10 to 80 weight percent of an alkanol having 2 or 3 carbon atoms; about 50 to 80 mole percent of the carboxy groups of the carboxymethyl cellulose acetate butyrate are neutralized with an alkanolamine base having a molecular weight of 45 to 200; and the sulfonate-containing, linear polyester has an Inherent viscosity of about 0.24 to 0.38 dL/g and is comprised of:
   (i) diacid monomer residues comprising about 74 to 84 mole percent isophthalic acid residues and about 16 to 26 mole percent 5-sodiosulfoisophthalic acid residues; and
   (ii) dial monomer residues comprising about 45 to 90 mole percent diethylene glycol residues and about 55 to 10 mole percent ethylene glycol residues, 1,4-cyclohexanedimethanol residues or mixtures thereof.

3. A hair grooming composition according to claim 1 wherein the $C_2$–$C_4$ alkanoate ester of carboxy($C_1$–$C_3$-alkyl) cellulose component is a carboxymethyl cellulose acetate propionate having an inherent viscosity of 0.30 to 0.60 dL/g, a degree of substitution per anhydroglucose unit of hydroxyl of 0.10 to 0.70, a degree of substitution per anhydroglucose unit of propionyl of 1.1 to 2.55, and a degree of substitution per anhydroglucose unit of acetyl is 0.1 to 0.9; the liquid vehicle comprises about 20 to 90 weight percent water and about 10 to 80 weight percent of an alkanol having 2 or 3 carbon atoms; about 50 to 80 mole percent of the carboxy groups of the carboxymethyl cellulose acetate propionate are neutralized with an alkanolamine base having a molecular weight of 45 to 200; and the sulfonate-containing, linear polyester has an inherent viscosity of about 0.24 to 0.38 dL/g and is comprised of:
   (i) diacid monomer residues comprising about 74 to 84 mole percent isophthalic acid residues and about 16 to 26 mole percent 5-sodiosulfoisophthalic acid residues; and
   (ii) diol monomer residues comprising about 45 to 90 mole percent diethylene glycol residues and about 55 to 10 mole percent ethylene glycol residues, 1,4-cyclohexanedimethanol residues or mixtures thereof.

* * * * *